(12) United States Patent
Fell

(10) Patent No.: US 9,375,567 B2
(45) Date of Patent: *Jun. 28, 2016

(54) DEVICES AND METHODS FOR VISUALLY INDICATING THE ALIGNMENT OF A TRANSCUTANEOUS ENERGY TRANSFER DEVICE OVER AN IMPLANTED MEDICAL DEVICE

(71) Applicant: Greatbatch Ltd., Clarence, NY (US)

(72) Inventor: Roger B. Fell, Avon Lake, OH (US)

(73) Assignee: Nuvectra Corporation, Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/703,961

(22) Filed: May 5, 2015

(65) Prior Publication Data
US 2015/0231392 A1 Aug. 20, 2015

Related U.S. Application Data

(63) Continuation of application No. 14/249,425, filed on Apr. 10, 2014, now Pat. No. 9,031,666, which is a continuation of application No. 13/185,636, filed on Jul. 19, 2011, now Pat. No. 8,700,175.

(51) Int. Cl.
*A61N 1/00* (2006.01)
*A61N 1/08* (2006.01)
*A61N 1/378* (2006.01)

(52) U.S. Cl.
CPC .............. *A61N 1/08* (2013.01); *A61N 1/3787* (2013.01)

(58) Field of Classification Search
CPC ... A61N 1/37; A61N 1/3787; A61N 1/37247; H02J 5/005; H02J 5/025
See application file for complete search history.

(56) References Cited

U.S. PATENT DOCUMENTS

| 5,991,665 | A | 11/1999 | Wang et al. |
| 6,009,878 | A | 1/2000 | Weijand et al. |
| 6,088,619 | A * | 7/2000 | Hein .................. A61N 1/08 607/61 |

(Continued)

FOREIGN PATENT DOCUMENTS

| WO | WO 2010/042056 | 4/2010 |
| WO | WO 2010/042057 | 4/2010 |
| WO | WO 2010/059097 | 5/2010 |

OTHER PUBLICATIONS

European Search Report received in corresponding European Application No. 12176586.1, dated Oct. 12, 2012, 9 pages.

*Primary Examiner* — Robert N Wieland
(74) *Attorney, Agent, or Firm* — Haynes and Boone, LLP; Eric Q. Li

(57) ABSTRACT

The present disclosure involves a charging system for charging an implanted medical system. The charging device includes a replenishable power supply. The charging device includes a coil assembly electrically coupled to the power supply. The coil assembly includes a primary coil and a plurality of sense coils positioned proximate to the primary coil. The charging device includes electrical circuitry operable to: measure an electrical parameter of the coil assembly; and determine a position of the coil assembly relative to a position of the implanted medical device based on the measured electrical parameter. The charging device includes a visual communications interface operable to: receive an input from the electrical circuitry; and visually display on a screen the position of the coil assembly relative to the position of the implanted medical device based on the input received from the electrical circuitry.

20 Claims, 10 Drawing Sheets

(56) References Cited

U.S. PATENT DOCUMENTS

| | | |
|---|---|---|
| 6,138,681 A | 10/2000 | Chen et al. |
| 7,286,880 B2 | 10/2007 | Olson et al. |
| 7,486,048 B2 | 2/2009 | Tsukamoto et al. |
| 7,774,069 B2 | 8/2010 | Olson et al. |
| 7,932,696 B2 | 4/2011 | Peterson |
| 8,000,800 B2 | 8/2011 | Takeda et al. |
| 8,005,547 B2 | 8/2011 | Forsberg et al. |
| 8,010,205 B2 | 8/2011 | Rahman et al. |
| 8,311,638 B2 | 11/2012 | Aghassian |
| 8,321,027 B2 | 11/2012 | Mozzi et al. |
| 8,473,066 B2 | 6/2013 | Aghassian et al. |
| 8,965,523 B2 | 2/2015 | Forsell |
| 2007/0270921 A1 | 11/2007 | Strother et al. |
| 2010/0137948 A1 | 6/2010 | Aghassian et al. |
| 2010/0201315 A1 | 8/2010 | Oshimi et al. |
| 2014/0012352 A1* | 1/2014 | Aghassian ............ A61N 1/3787 607/61 |
| 2014/0176063 A1* | 6/2014 | Forsell ................... H02J 7/025 320/108 |

\* cited by examiner

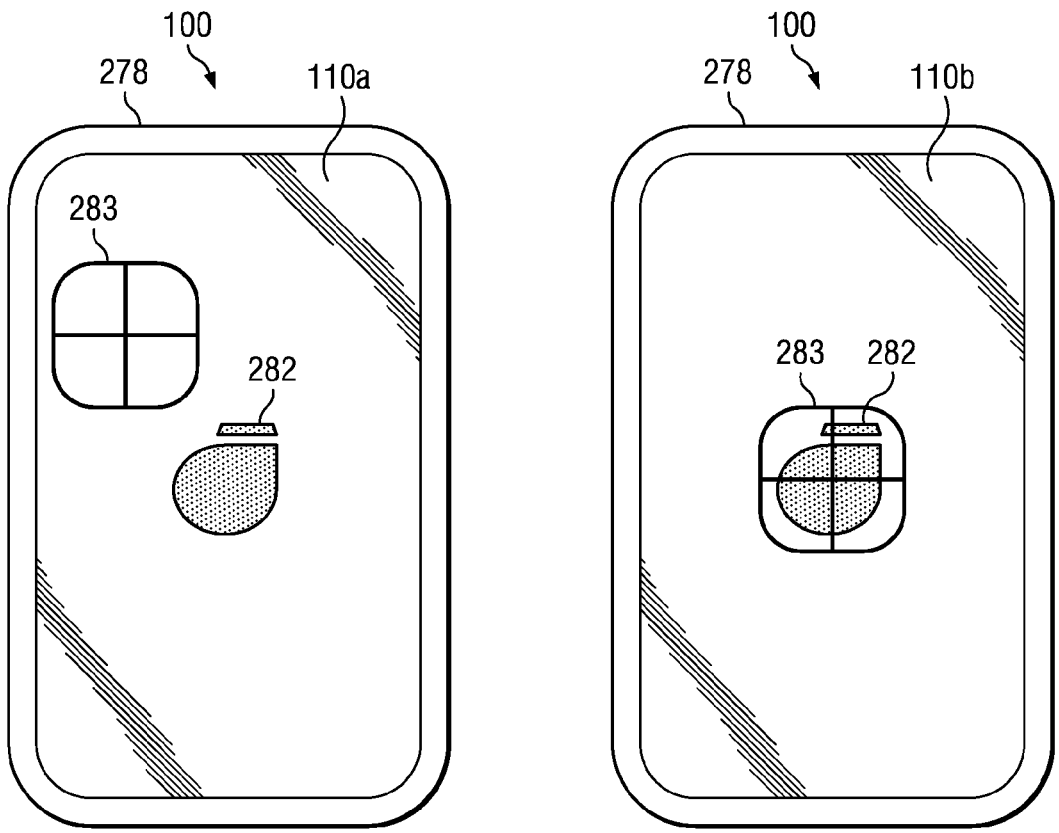
*Fig. 9A*  *Fig. 9B*
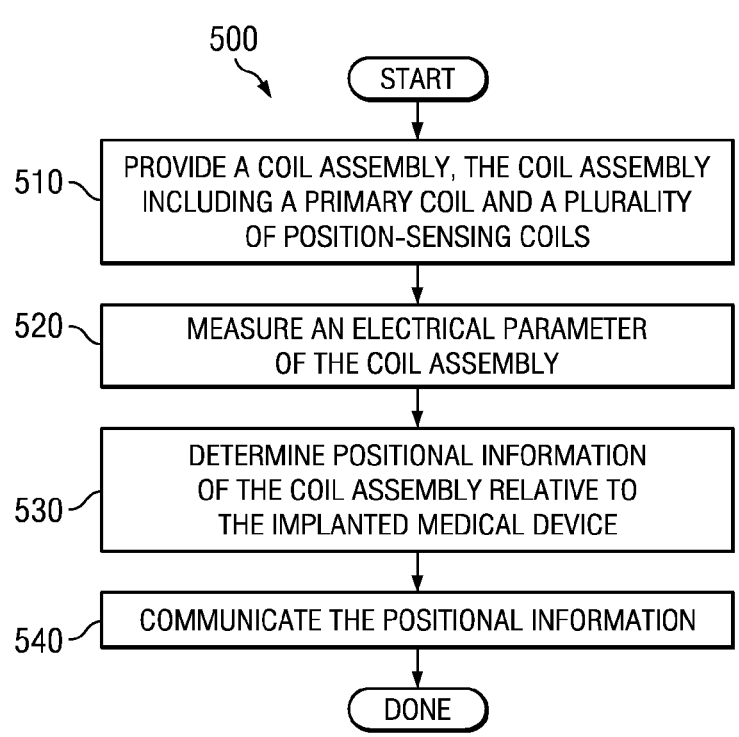
*Fig. 12*

DEVICES AND METHODS FOR VISUALLY INDICATING THE ALIGNMENT OF A TRANSCUTANEOUS ENERGY TRANSFER DEVICE OVER AN IMPLANTED MEDICAL DEVICE

PRIORITY DATA

The present application is a continuation application of U.S. patent application Ser. No. 14/249,425, filed on Apr. 10, 2014, now U.S. Pat. No. 9,031,666 issued May 12, 2015, which is a continuation application of U.S. patent application Ser. No. 13/185,636, filed on Jul. 19, 2011, now U.S. Pat. No. 8,700,175 issued Apr. 15, 2014, the disclosures of each are hereby incorporated by reference in their entirety.

BACKGROUND

Implantable medical devices for producing a therapeutic result in a patient are well known. The implanted medical device often requires electrical power to perform its therapeutic function. This electrical power is derived from a power source. There are many kinds of powered, implantable medical devices that are powered by an external power source. It is recognized that other implantable medical devices are envisioned which also utilize energy transferred from or delivered by an external source.

By way of example, one type of powered, implantable medical device is a neurostimulation device. Neurostimulator devices, such as implantable pulse generators (hereinafter "IPGs"), are battery-powered devices that deliver therapy in the form of electrical stimulation pulses to treat symptoms and conditions, such as chronic pain, urinary incontinence, Parkinson's disease, deafness, or epilepsy, for example. IPGs deliver neurostimulation therapy via leads that include electrodes located proximate to the muscles and nerves of a patient. Treatments may require two external devices: a neurostimulator controller and a neurostimulation device charger. Neurostimulator controllers are frequently used to adjust treatment parameters, select programs, and download/upload treatment information into/from the implantable device. Neurostimulation device chargers are used to transcutaneously recharge batteries or capacitors in the implanted device.

Transcutaneous transmission of energy from an external transmitter to an internal receiver is known in the prior art. Several implantable medical devices, including an IPG, employ a replenishable power source such as a storage capacitor or a rechargeable battery. This replenishable power source can be recharged when necessary using transcutaneous energy transfer (hereinafter "TET") from an external power source, i.e., energy is transferred non-invasively through the skin via electromagnetic communication between an external transmitter coil and an implanted receiver coil. TET involves the process of inductive coupling between two coils positioned in close proximity to each other on opposite sides of a cutaneous boundary. The external transmitter coil, composed of a plurality of wire windings, is energized by a source of alternating electrical current. This flow of electrical current in the external transmitter coil induces a corresponding current in the windings of the internal receiver coil. This resultant current can be applied to recharge the battery of the implanted medical device, or, in addition, can directly energize the IPG. Optimum transcutaneous energy transfer efficiency is achieved when the external transmitter coil is disposed on the patient's skin, directly opposite the implanted receiver coil, with a minimum separation distance between the external transmitter coil and the implanted receiver coil.

Though TET provides the advantage of non-invasive recharging of an IPG, TET is not without certain shortcomings. For example, the efficiency of transcutaneously inducing a current in the implanted coil is detrimentally affected if the external TET coil and implanted coil are not properly aligned. Though the operator of the TET device may use the visual or tactile signs of implantation to approximate the location of the IPG, precise alignment of the TET coil and charging coil is extremely difficult without the aide of an alignment indicator. Because there is no physical connection between the external TET device and the IPG to provide feedback, ascertaining whether the efficiency of energy transfer is maximized is problematic.

Even if the TET device is properly aligned with the IPG at the initiation of the charging process, the correct alignment of the devices may not endure over the period of time required for energy transfer. Energy transfer can continue for a significant period of time, ranging from several minutes to hours, before the IPG is fully recharged. During this time, it is often impracticable for the external TET coil to maintain ideal alignment with the IPG receiver coil. The patient's movement may cause the external TET coil to move, thereby misaligning the TET coil with the IPG receiver coil and reducing the efficiency of energy transfer. Therefore, it would be advantageous to provide a TET device that could indicate the real time alignment (or misalignment) of the devices and visually direct the operator toward regaining optimal alignment, thereby increasing the efficiency of energy transfer and decreasing the amount of time required for the IPG charging process.

In addition, prolonged exposure to the electromagnetic fields and heat generated by the external TET coil and the IPG can result in damage to human skin and adjacent tissues. The resulting damage generally increases with the length of exposure time. Therefore, it is desirable to limit the amount of time required to recharge the battery of an IPG using a TET device. If the devices are poorly aligned, the efficiency of transcutaneous energy transfer is reduced and the length of time required to charge the IPG is increased, thus extending the patient's exposure time to electromagnetic radiation and heat. Reducing the exposure time by improving device alignment would reduce potential tissue injury. Therefore, though existing TET devices have been generally adequate for their intended purposes, they are not entirely satisfactory in every aspect.

SUMMARY

One of the broader forms of the present disclosure involves a charging device for charging an implanted medical device. The charging device includes a replenishable power supply; a coil assembly electrically coupled to the power supply, the coil assembly including a primary coil and a plurality of sense coils positioned proximate to the primary coil; electrical circuitry operable to measure an electrical parameter of the coil assembly and determine a position of the coil assembly relative to the implanted medical device based on the measured electrical parameter; and a communications interface operable to convey the position of the coil assembly relative to the implanted medical device.

In an embodiment, the communications interface includes a display unit that is operable to visually display the position of the coil assembly relative to the implanted medical device.

In an embodiment, the communications interface is operable to give directional instructions to a user to align the coil assembly with the implanted medical device.

In an embodiment, the power supply, the electrical circuitry, and the communications interface are integrated into a charger unit; and the charger unit is electrically coupled to the coil assembly through a conductive cable.

In an embodiment, the sense coils are located in different layers of a substrate and are aligned with one another.

In an embodiment, at least two of the sense coils are perpendicularly oriented with respect to each other.

In an embodiment, the primary coil is located over the sense coils.

In an embodiment, the measured electrical parameter includes an electrical voltage of at least one of the sense coils.

In an embodiment, the electrical circuitry is operable to translate the electrical parameter into a positional displacement of the coil assembly relative to the implanted medical device.

In an embodiment, the electrical circuitry contains: an amplifier section that is coupled to at least one of the sense coils; a rectifier section that is coupled to the amplifier section; a filter section that is coupled to the rectifier section; and a comparators section that is coupled to the filter section.

Another one of the broader forms of the present disclosure involves a medical charging system. The charging system includes a coil assembly structure that includes: a plurality of position-sensing coils; and a primary coil disposed proximate to the position-sensing coils; circuitry that is electrically coupled to the coil assembly structure, the circuitry being configured to: make measurements of electrical characteristics of the position-sensing coils; and translate the measurements into a location displacement of the coil assembly structure; and a visual display configured to display the location of the coil assembly.

In an embodiment, the medical charging system further includes a medical device implanted in a body tissue, and the circuitry that is electrically coupled to the coil assembly structure is configured to translate the electrical characteristics of the position-sensing coils into the location displacement of the coil assembly structure with respect to the medical device.

In an embodiment, the medical device contains a coil, and the circuitry is configured to translate the electrical characteristics of the position-sensing coils into relative alignment between the coil assembly structure and the coil of the medical device.

In an embodiment, the visual display is configured to display a location of the medical device.

In an embodiment, the visual display is configured to give directional movement instructions for bringing the coil assembly structure into alignment with the medical device.

In an embodiment, the electrical characteristics are induced voltages at the position-sensing coils in response to a magnetic flux.

In an embodiment, the circuitry is configured to translate a voltage in each position-sensing coil into a respective locational displacement of the coil assembly structure in one of a plurality of different directions.

In an embodiment, the circuitry is configured to detect a zero crossing event.

In an embodiment, the position-sensing coils have different orientations and are substantially concentrically located.

In an embodiment, the medical charging system further includes a power source that is electrically coupled to the coil assembly structure.

In an embodiment, the circuitry and the visual display are implemented inside a handheld control device, and the handheld control device is electrically coupled to the coil assembly structure through a conductive cable.

One more of the broader forms of the present disclosure involves an apparatus for charging a medical device implanted in a body tissue. The apparatus includes: coil assembly means for transcutaneously delivering electrical power to the implanted medical device, wherein the coil assembly means includes a primary coil and first and second position-sensing coils located adjacent to the primary coil; circuitry means for gathering electrical data associated with the coil assembly means and for obtaining locational information of the coil assembly means relative to the implanted medical device based on the gathered electrical data; and communication means for communicating the locational information of the coil assembly means and for giving directional instructions based on the locational information.

In an embodiment, the communication means includes visual display means for visually indicating an extent of alignment between the coil assembly and the implanted medical device.

In an embodiment, the communication means includes means for instructing a user on how to move the coil assembly means in order to achieve alignment between the coil assembly means and the implanted medical device.

In an embodiment, the electrical data includes voltages in the first and second position-sensing coils, and the circuitry means includes means for translating the voltages into physical displacements of the coil assembly means in different first and second directions, respectively.

In an embodiment, the circuitry means includes: amplifying means for amplifying a signal received from at least one of the first and second position-sensing coils; rectifying means for converting an alternating current (AC) portion of an output from the amplifying means to a direct current (DC) portion; filtering means for filtering an output of the rectifying means; and comparator means for detecting a zero-crossing event.

In an embodiment, the apparatus further includes a power supply means for supplying power to the coil assembly means.

In an embodiment, the apparatus further includes: housing means for housing the power supply means, the circuitry means, and the communication means; and cabling means for coupling the housing means with the coil assembly means.

Yet another one of the broader forms of the present disclosure involves a method for charging a medical device implanted in a body tissue. The method includes: providing a coil assembly, the coil assembly including a primary coil and a plurality of position-sensing coils; measuring an electrical parameter of the coil assembly; determining, in response to the measuring, positional information of the coil assembly relative to the implanted medical device; and communicating the positional information.

In an embodiment, the providing is carried out in a manner such that: the primary coil is located over the position-sensing coils; and the position-sensing coils are concentrically-located and have different orientations.

In an embodiment, the measuring includes measuring a first voltage at a first one of the position-sensing coils and measuring a second voltage at a second one of the position-sensing coils.

In an embodiment, the determining includes: translating the first voltage into a displacement of the coil assembly along a first axis; and translating the second voltage into a displacement of the coil assembly along a second axis different from the first axis.

In an embodiment, the communicating includes visually displaying positional information of the coil assembly and positional information of the implanted medical device.

In an embodiment, the communicating includes giving directional instructions for moving the coil assembly to achieve alignment with the implanted medical device.

In an embodiment, the method further includes transcutaneously charging the implanted medical device through the coil assembly.

Further aspects, forms, embodiments, objects, features, benefits, and advantages of the present disclosure shall become apparent from the detailed drawings and descriptions provided herein.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 4 illustrates the TET device being moved in a plane parallel to the skin surface towards the implantable pulse generator. FIG. 5 illustrates the TET device aligned with the implantable pulse generator.

FIG. 7A represents the voltage relative to the displacement in the X-axis, and FIG. 7B represents the voltage relative to the displacement in the Y-axis.

FIGS. 9A and 9B are top views of a TET device, showing the display screen. FIG. 9A illustrates the display when the TET device and the implantable medical device are not in alignment, and FIG. 9B illustrates the display when the TET device and the implantable medical device are in alignment.

FIG. 12 is a flowchart illustrating a method of operation of the TET device.

DETAILED DESCRIPTION

Figure 1:
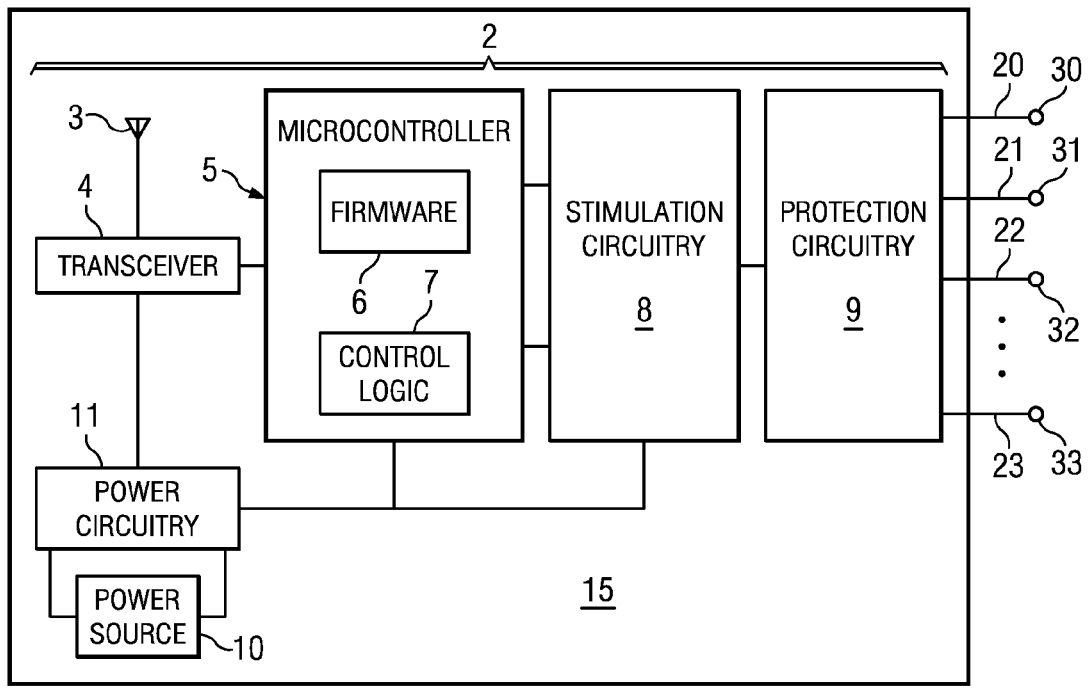
FIG. 1 is a diagrammatic view of a neurostimulator device.

For the purposes of promoting an understanding of the principles of the present disclosure, reference will now be made to the embodiments, or examples, illustrated in the drawings and specific language will be used to describe the same. It will nevertheless be understood that no limitation of the scope of the present disclosure is thereby intended. Any alterations and further modifications in the described embodiments, and any further applications of the principles of the present disclosure as described herein are contemplated as would normally occur to one skilled in the art to which the present disclosure relates.

FIG. 1 is a simplified diagrammatic view of an embodiment of a neurostimulator device 2. The neurostimulator device 2 includes an antenna 3 and a transceiver 4 coupled to the antenna 3. The antenna 3 is capable of sending signals to an external device and receiving signals from the external device. The transceiver 4 contains transmitter circuitry and receiver circuitry that together carry out bidirectional digital communication with the external device. In an embodiment, the signals are transmitted and received at Radio Frequencies (RF).

The neurostimulator device 2 includes a microcontroller 5 that is coupled to the transceiver 4. The microcontroller 5 runs firmware 6, which is a control program, to operate control logic 7. The firmware 6 includes dedicated low-level software code that is written for a specific device, in this case the control logic 7. The control logic 7 includes digital circuitry that is implemented using a plurality of transistors, for example Field Effect Transistors (FETs). In the embodiment shown in FIG. 1, the firmware 6 and the control logic 7 are integrated into the microcontroller 5. In alternative embodiments, the firmware 6 or the control logic 7 may be implemented separately from the microcontroller 5.

The neurostimulator device 2 includes stimulation circuitry 8 that receives the output of the microcontroller 5. In an embodiment, the stimulation circuitry 8 is implemented on an Application Specific Integrated Circuit (ASIC) chip. The stimulation circuitry 8 includes electrical pulse generation circuitry. Based on the output of the microcontroller 5, the electrical pulse generation circuitry generates electrical pulses to a target tissue area.

The neurostimulator device 2 also includes protection circuitry 9 that is coupled to the output of the stimulation circuitry 8. In an embodiment, the protection circuitry 9 includes direct-current (DC) blocking capacitors and other electrical transient suppression components. The protection circuitry 9 protects the patient's tissue from unwanted electrical signals. The protection circuitry 9 also protects the neurostimulator device 2 from undesirable external electrical signals that may be generated by events such as electrostatic discharge, defibrillation, or electrocautery.

The neurostimulator device 2 may also include a power source 10 and power circuitry 11. In an embodiment, the power source 10 includes a battery. In another embodiment, the power source 10 includes a coil that is a part of a transformer (not illustrated). In that case, the transformer has a charging coil that is external to the neurostimulator device 2 and inductively coupled to the coil of the power source 10. The power source 10 therefore obtains energy from such inductive coupling to the charging coil. In some embodiments, the power source 10 may also include both a battery and a coil. The charging process may be done using an external transcutaneous charger, which will be discussed later in more detail.

The power source 10 provides electrical power to the power circuitry 11. The power circuitry 11 is coupled to the transceiver 4, the microcontroller 5, and the stimulation circuitry 8. The power circuitry 11 supplies and regulates power to these coupled circuitries. In an embodiment, the power circuitry 11 is implemented on an ASIC device.

In an embodiment, the antenna 3, the transceiver 4, the microcontroller 5, the stimulation circuitry 8, the protection circuitry 9, the power source 10, and the power circuitry 11 are all contained within a hermetically-sealed housing or can 15, which may also be considered a part of the neurostimulator device 2. The housing 15 may be made from titanium or another suitable durable and/or conductive material that is compatible with human implantation.

A plurality of conductors (also referred to as lead wires) 20-23 run from the internal circuitry through hermetic feedthroughs to one or more connectors mounted on the hermetic enclosure 15. The lead wires 20-23 plug into, and are removable from, those connectors. In another embodiment, the connectors are eliminated, and the lead wires 20-23 are directly and permanently connected to the hermetic feedthroughs. In some embodiments, the neurostimulator incorporates the electrode contacts into its outer surface. In such embodiments, the hermetic feedthroughs may be designed to incorporate an electrode contact in the tissue-facing side of each feedthrough, or may be designed to have insulated lead wires built into the neurostimulator housing, exterior to the hermetically-sealed enclosure 15, that carry signals between the hermetic feedthroughs and the electrode contacts. It is understood that the lead wires 20-23 are shown here merely as examples, and that an alternative number of lead wires may be implemented, for example 16 or 24 lead wires.

Electrode contacts 30-33 (also referred to as electrodes) are coupled to the lead wires 20-23. The electrode contacts 30-33 are implanted in different areas of a patient's body, where electrical stimulation is desired. These different areas may be within a few inches of one another. In an embodiment, an exterior portion of the housing 15 is also used as an electrode contact. In another embodiment, one or more electrode contacts can be incorporated into the design of a non-conductive housing 15. In any case, the electrode contacts may also be considered parts of the neurostimulator system.

In an embodiment, the neurostimulator device 2 is implemented as an IPG having all the components shown in FIG. 1 that is surgically implanted inside the patient's body. Outside the body, the neurostimulator device 2 can be programmed using a Clinician Programmer (not illustrated) or a Patient Programmer (not illustrated). The Clinician Programmer is used by medical personnel to configure the neurostimulator device 2 for the particular patient and to define the particular electrical stimulation therapy to be delivered to the target area of the patient's body. The Patient Programmer is used by the patient himself to control the operation of the neurostimulator device 2. For example, the patient can alter one or more parameters of the electrical stimulation therapy, depending on the programming and the configuration of the neurostimulator device 2 as set by the Clinician Programmer.

In alternative embodiments, the neurostimulator device 2 can be implemented as an External Pulse Generator (EPG). In that case, only a portion of the neurostimulator system (for example the electrode contacts 30-33 and/or portions of the lead wires 20-23) is implanted inside the patient's body, while the neurostimulator device 2 remains outside the body. Other than their exact placements, the functionalities and the operations of the IPG and the EPG are similar. Thus, in the following discussions, IPG may be used to refer to both an IPG and an EPG. A medical device manufacturer may manufacture and provide the neurostimulator device 2 to a clinician or a patient. Clinicians may also provide the neurostimulator device to a patient. Some of the functionalities of the microcontroller 5 may be pre-programmed by the manufacturer or may be programmed by the clinician or patient.

The neurostimulator device 2 is capable of varying the amount of electrical stimulation delivered to each of the electrode contacts 30-33. This is carried out by creating individually controllable electrical paths, or channels. Each channel includes one of the electrode contacts 30-33, one of the lead wires 20-23 coupled to the electrode contact, and respective portions of the protection circuitry 9 and respective portions of the stimulation circuitry 8.

Figure 2:
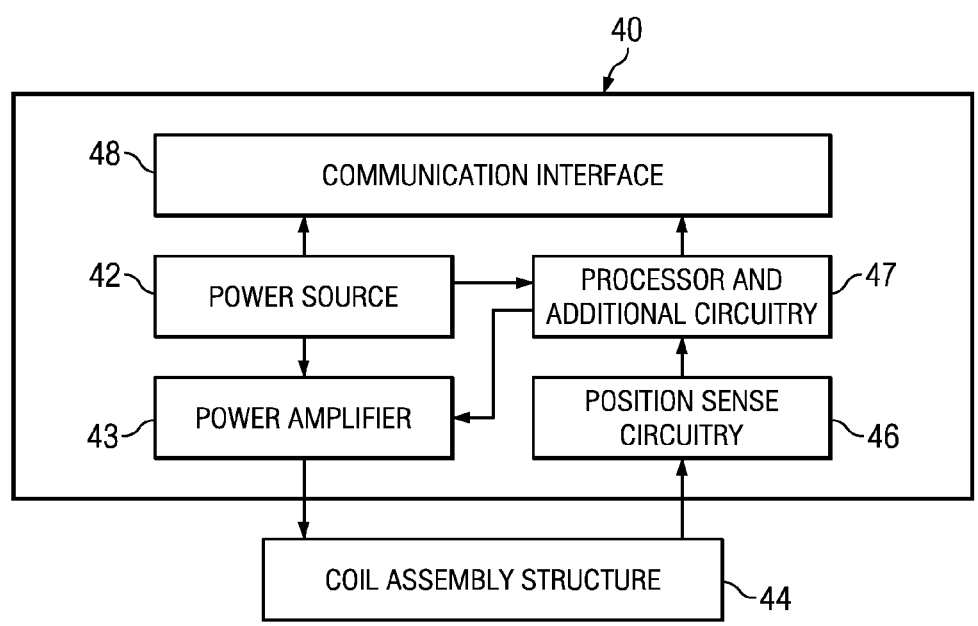
FIG. 2 is a diagrammatic view of an external power charging device.

As discussed above, an external charging device may be used to provide electrical power transcutaneously to the power source 10. FIG. 2 is a simplified diagrammatic view of such external charging device 40. The external charging device 40 (also referred to as an external device charger or a transcutaneous energy transfer device) includes a power source 42, a power amplifier 43, a coil assembly structure 44, position-sensing circuitry 46, processor and additional circuitry 47, and a communication interface 48. The power source 42 includes a replenishable power supply, for example a rechargeable battery or a replaceable battery. The output of the power source 42 is amplified by the power amplifier 43. The power source 42 (in conjunction with the power amplifier 43) delivers electrical power or electrical energy to the coil assembly structure 44, the position-sensing circuitry 46, the processor and additional circuitry 47, and the communication interface 48.

In the illustrated embodiment, the power source 42, the power amplifier 43, the position-sensing circuitry 46, the processor and additional circuitry 47, and the communication interface 48 are housed within the charger device 40. The coil assembly structure 44 may be implemented physically separate from the charger device 40, as is shown in FIG. 2. In such embodiments, the coil assembly structure 44 may be coupled to the charger 40 through a conductive cable. In alternative embodiments, however, the coil assembly structure 44 may be implemented inside the charger 40.

In an embodiment, the coil assembly structure 44 includes a core (e.g., a toroid ferrite core), a primary coil that circumferentially surrounds the core, and two secondary position-sensing coils that are disposed over the core and the primary coil. It is understood that alternative embodiments of the coil assembly structure may not have a core. In an embodiment, the primary coil is a multi-layered spiral coil. In an embodiment, the two secondary position-sensing coils each have a double-D shape, are substantially identical in size, are substantially concentrically disposed over one another, and have substantially perpendicular orientations. The coil assembly structure 44 can be used to detect alignment with the coil inside the neurostimulator device 2 of FIG. 1. Thus, the coil assembly structure 44 may also be referred to as a coil positioning system (CPS). When the coil assembly structure 44 and the coil of the neurostimulator device 2 are aligned, transcutaneous energy transfer is optimized. The coil assembly structure 44 and the alignment detection process will be discussed in more detail below.

The position-sensing circuitry 46 includes a plurality of active and/or passive components, such as transistors, resistors, capacitors, and inductors. The position-sensing circuitry 46 is operable to correlate a physical displacement or movement of the coil assembly structure 44 relative to the internal coil of the neurostimulator device 2 (of FIG. 1) by measuring electrical characteristics associated with the coil assembly structure 44, for example a voltage in one of the secondary position-sensing coils. As such, the position-sensing circuitry 46 can be used to ascertain locational information of the coil assembly structure 44. Such locational information can be processed by the processor and additional circuitry 47 and communicated to a user through the communication interface 48. In an embodiment, the communication interface 48 includes a visual display unit, such as a flat panel screen. In other embodiments, the communication interface 48 may include other means of communication, such as one or more audio or tactile components. For example, the communication interface 48 may audibly instruct an operator where or how to move the coil assembly structure 44 in order to achieve optimum alignment. Based on the information communicated through the communication interface 48, an operator can adjust the alignment between the coil assembly structure 44 with the internal coil of the neurostimulator device 2 until the alignment is optimum for transcutaneous energy transfer. The position-sensing circuitry 46 and the communication interface 48 will be discussed in more detail below.

Figure 3:
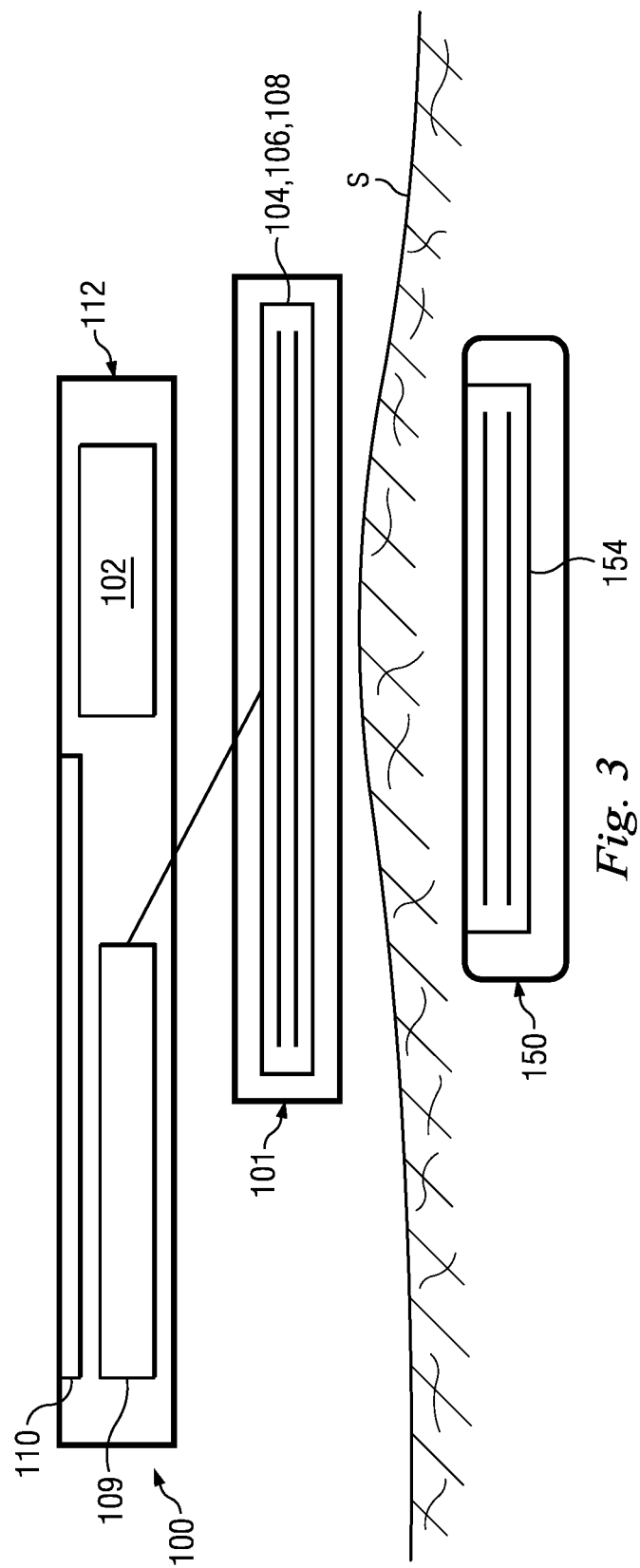
FIG. 3 is a partial cross-sectional side view of a transcutaneous energy transfer (hereinafter "TET") device, a coil assembly positioned slightly above the skin and an implantable pulse generator implanted subcutaneously.

FIG. 3 illustrates a simplified fragmentary cross-sectional side view of a transcutaneous energy transfer device (TET device) 100, a coil assembly 101 coupled to the TET device 100, and an implantable pulse generator (IPG) 150. The TET device 100 is implemented as an embodiment of the external charging device 40 shown in FIG. 2, the coil assembly 101 is implemented as an embodiment of the coil assembly structure 44 of FIG. 2, and the IPG 150 is implemented as an embodiment of the neurostimulator device 2 shown in FIG. 1. Those of ordinary skill in the art will understand, however, that the IPG 150 is not limited to a neurostimulator. In other embodiments, the IPG 150 may be a different type of IPG, including, for example, a pacemaker, a defibrillator, a trial stimulator or any other type of medical device.

As discussed above, several rechargeable medical devices implanted in the human body require power (or energy) to be supplied transcutaneously from a TET device to the implantable medical device. This energy transfer is typically provided via an inductive link consisting of an external transmitter coil that generates an alternating electromagnetic field and a receiver coil in the implant that converts the received electromagnetic energy into electrical energy to generate power. The power that is delivered over the transcutaneous link is used by the implant to power its internal electronics, recharge a battery, or both. The IPG 150 herein is structurally configured and arranged for wireless programming and control through the skin of the patient. Accordingly, it may include a transceiver (e.g., transceiver 4 of FIG. 1) capable of communicating with external programming and control devices, such as the TET device 100 and a human operator. It also includes a rechargeable power source (e.g., power source 10 of FIG. 1) that can be configured to be wirelessly recharged through the patient's skin when the coil assembly 101 connected to the TET device 100 is externally placed in the proximity of the IPG 150.

In the embodiment shown in FIG. 3, the IPG includes an IPG charging coil 154 used to recharge the IPG's rechargeable power source. Those of ordinary skill in the art will recognize that other components may also be included within an IPG, such as a transceiver to transmit/receive data to/from an external controller, sensors, pulse generation circuitry, microcontrollers, power conditioning circuitry, and protection circuitry.

The IPG charging coil 154 can receive power while the IPG 150 is implanted in a patient through the use of the TET device 100. The rechargeable power source within the IPG 150 may be any of a variety of power sources including a chemically-based battery or a capacitor. The rechargeable power source may also be a well known lithium ion battery. The TET coil 104 induces in the position-sensing coils 106, 108 an oscillating or alternating current while also inducing current in the charging coil 154 when the TET coil 104 is placed in the proximity of the charging coil 154.

As shown in FIG. 3, the TET device 100 and the coil assembly 101 are located outside the patient in which the IPG 150 is implanted. The coil assembly 101 is positioned above but near the external surface of the skin S, slightly lateral to the placement of the IPG 150, which is shown implanted beneath the skin S of the patient. Although the TET device 100 is shown with a rectangular configuration, it should be understood that the TET device 100 may take any desired shape. Power is provided to the TET device 100 through a rechargeable battery 102. In the illustrated embodiment, a transcutaneous energy transfer coil (hereinafter "TET coil") 104 and two position-sensing coils 106 and 108 are disposed together within the coil assembly 101. A circuitry section 109 correlates electrical characteristics of the coil assembly 101 with any movement or physical displacement of the coil assembly 101 relative to the IPG 150. After computing the locational information of the coil assembly 101, the circuitry section 109 (which includes position-sensing circuitry) instructs a display screen 110 to communicate such locational information. The display screen 110 is disposed on the surface 112 of the TET device 100. In the embodiment shown, the display screen 110 can exhibit a visual representation of the alignment or relative disposition of the and the IPG 150 to an operator.

Figure 4:
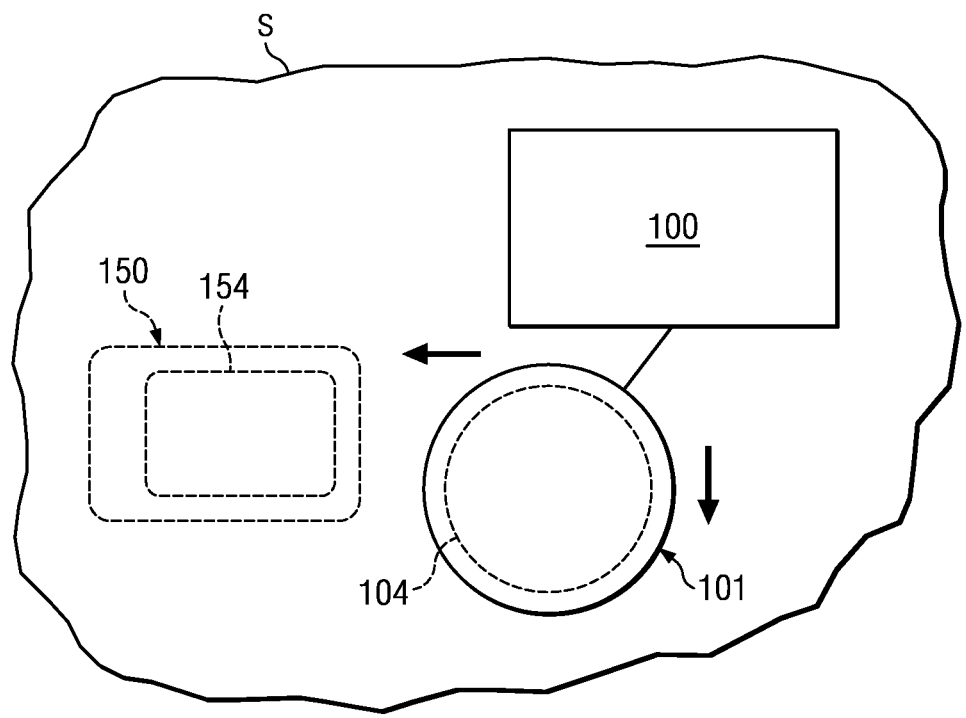
FIGS. 4 and 5 are top views of a TET device positioned slightly above the skin and an implantable pulse generator implanted subcutaneously.
Figure 5:
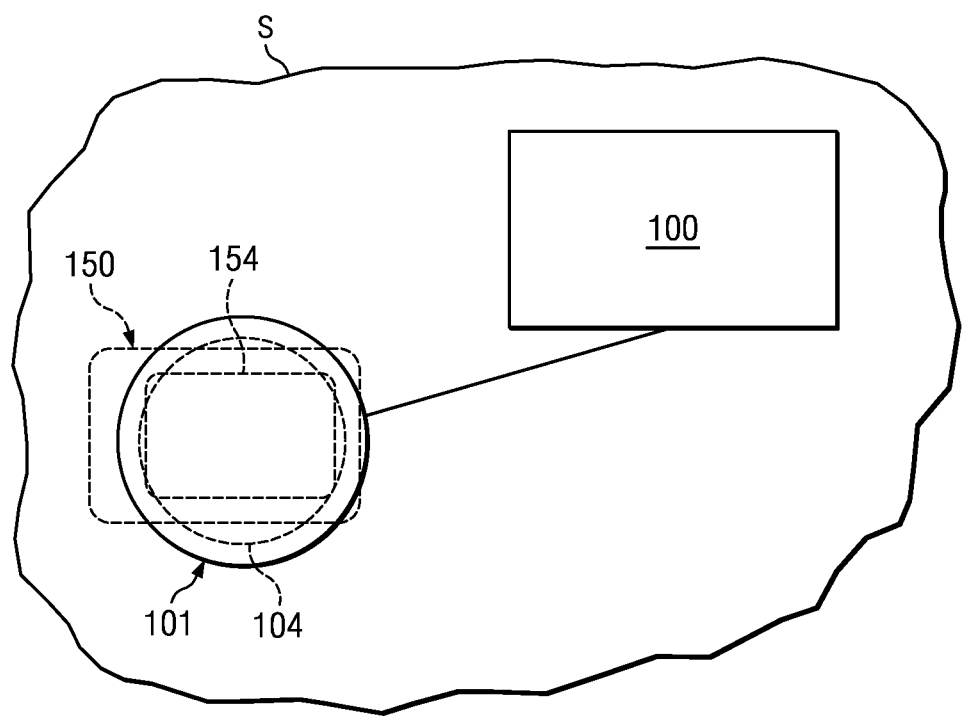

FIGS. 4 and 5 are simplified top views of the TET device 100, the coil assembly 101 that is positioned slightly above the skin, and an IPG 150 implanted subcutaneously under a patient's skin. Efficient energy transfer is dependent on the proper co-axial alignment of the TET coil 104 (of the coil assembly 101) with the IPG's charging coil 154. FIG. 4 illustrates the coil assembly 101 being moved in a plane parallel to the skin surface towards the IPG 150. Implantable medical devices such as the illustrated IPG 150 are typically implanted subcutaneously at depths, depending upon the type of device, ranging from 0.5 centimeter to 2.5 centimeters. After the IPG 150 has been surgically implanted in the patient, the location of the implant is often discernable by a visual and/or tactile sign such as a scar, an indentation of the skin, or a bulging area of skin. Nevertheless, the precise position of the charging coil 154 within the IPG 150 is difficult to discern using only visual or tactile signs. Exacerbating the problem is the fact that the IPG coil 154 may not be centered within the IPG 150. In such a case, even if the TET coil 104 is properly aligned over the IPG 150, the TET coil 104 and the IPG coil 154 may still not be precisely aligned. Though the operator of the TET device 100 may use the visual or tactile signs of implantation to approximate the location of the IPG 150, precise alignment of the TET coil 104 and IPG coil 154 can be difficult.

FIG. 5 illustrates the coil assembly 101 substantially aligned with the IPG coil 154. When the coil assembly 101 (the TET coil 104, in particular) is centered over the IPG coil 154, the efficiency of the transcutaneous energy transfer between the TET coil 104 and the IPG coil 154 is maximized. Thus, the best performance of energy transfer is obtained when the two coils, the TET coil 104 and the IPG coil 154, are aligned as shown in FIG. 5, but this alignment is not easy to achieve because the exact position of the IPG coil 154 is often difficult to identify. Any misalignment between the two coils reduces the efficiency of the energy transfer because a smaller quantity of energy is being received by the IPG coil 154, resulting in the TET coil 104 needing to deliver more power to complete the recharging process, and potentially multiple charging sessions to achieve a full recharge.

For implanted devices, the efficiency at which energy is transcutaneously transferred is important. The inductive coupling of the TET coil 104 and the IPG coil 154 has a tendency to heat the surrounding tissue. Heat generated by the coil assembly 101 and the IPG 150 is lost into the surrounding tissue, causing an increase in the temperature of the surrounding tissue. Depending on the time required for the energy transfer, such a temperature increase may result in side effects ranging from mere discomfort to severe tissue lesions. The higher the efficiency of energy transfer, the more energy can be transferred while at the same time limiting the heating of surrounding tissue. The present disclosure may be used to facilitate the efficient alignment and charging of any cooperating pair of TET device 100 and implantable medical device. For example, the present TET device 100 could be used as a part of a system employing an implantable medical device such as a cardiac pacemaker, cardioverter, defibrillator, an implantable drug pump, or a nerve stimulator.

Figure 6A:
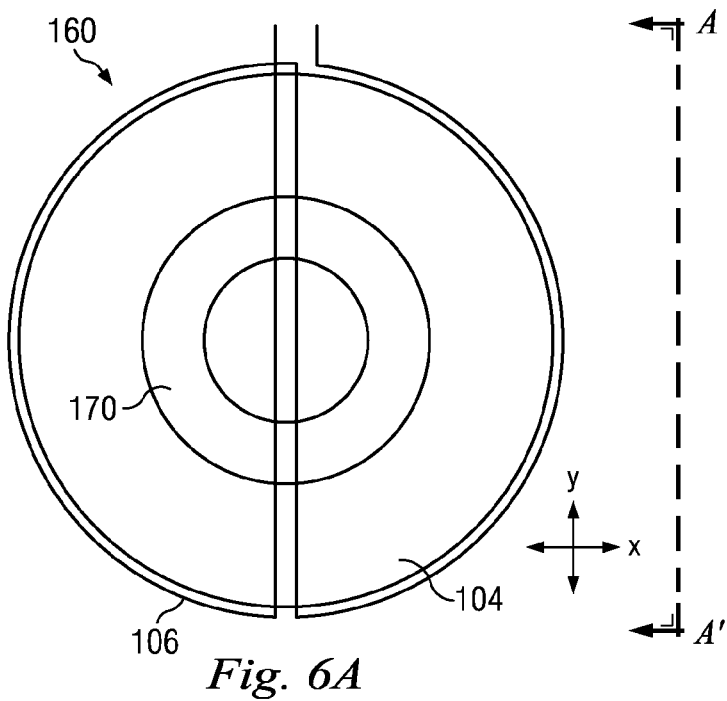
FIGS. 6A-6B are cut-away top views of a coil assembly comprising a transcutaneous energy transfer coil and positioning-sensing coils.
Figure 6B:
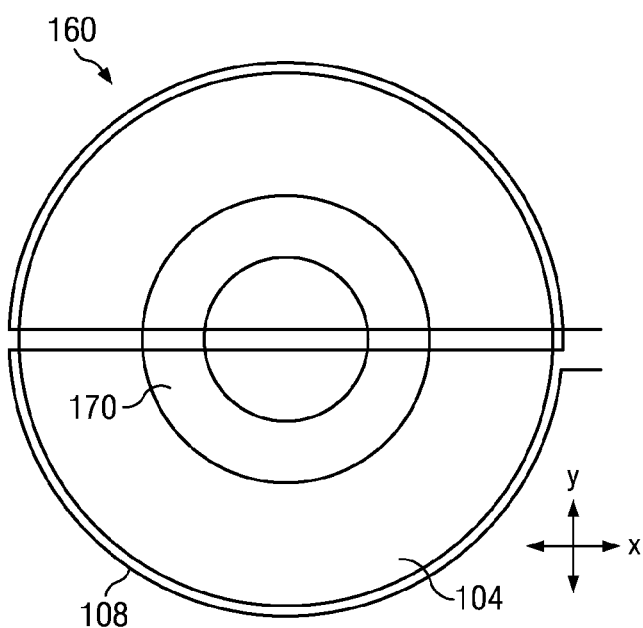

FIG. 6A-6B are cut-away top views of a coil assembly 160 comprising a TET coil 104 and two position-sensing coils 106 and 108. For the sake of visual clarity, the position-sensing coils 106 and 108 are shown separately, with the coil 106 being shown in FIG. 6A, and the coil 108 being shown in FIG. 6B. In an embodiment, the position-sensing coils 106 and 108 are substantially identical in size and shape and are situated such that the coils are concentric and perpendicularly oriented with each other. For example, the position-sensing coil 106 is oriented in an X-direction or an X-axis, and the position-sensing coil 108 is oriented in a Y-direction or a Y-axis. The position-sensing coils 106, 108 are each configured in a "Double D" winding shape, and are disposed in a manner such that they are centered against and overlaying the TET coil 104. It is envisioned that other sense coil arrangements can also be employed to provide alignment feedback.

In the present embodiment, the TET coil 104 is a three layer spiral comprising 13/12/10 turns of Litz wire 65/36. The TET coil 104 is shown circumferentially disposed around a toroid core 170. The toroid core 170 may comprise a ferrite core which increases the magnetic flux density to facilitate the energy transfer between the TET coil 104 and the IPG coil 154. Stated differently, the toroid core 170 helps to focus the electromagnetic energy generated by the TET coil 104 transcutaneously toward the IPG coil 154. Alternatively, the toroid core 170 could comprise other structures or materials, or could represent an air core.

Figure 6C:
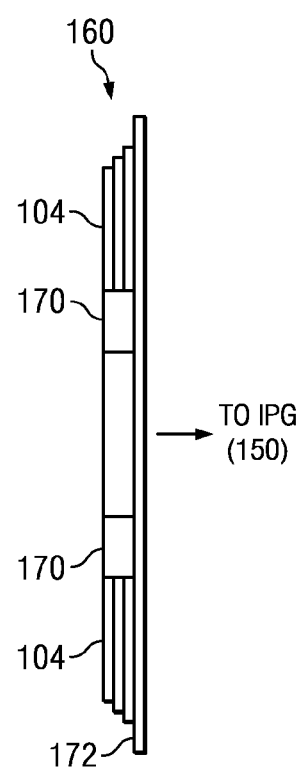
FIG. 6C is a cross-sectional view of the transcutaneous energy transfer coil of FIGS. 6A-6B.

FIG. 6C is a cross-sectional view of the coil assembly 160 of FIG. 6A taken from point A to point A'. The three layers of the TET coil 104, the toroid core 170, and a TET coil substrate 172 are diagrammed in FIG. 6C. The TET coil substrate 172 directly abuts and underlies the flat circular surface of the TET coil 104 that is configured to face the IPG 150. The TET coil substrate 172 contains a printed circuit board (PCB) with printed sense coils. In addition, the TET coil 104 could be integrated with or wound around other electronic components in the TET device 100.

The coil assembly 160 cooperates with the IPG 150 to detect optimum alignment of the TET coil 104 and the IPG coil 154. The TET coil 104 and the position-sensing coils 106 and 108 together function in a similar manner to a linear variable differential transformer (hereinafter "LVDT"), which can be used to measure linear displacement. An example LVDT has three solenoidal coils placed around a tube. The center coil is the primary coil and the two outer coils are the secondary coils. In an embodiment, the outer secondary coils are connected in reverse series. A cylindrical ferromagnetic core is attached to an object whose position is to be measured, and the core slides along the axis of the tube. An alternating current is driven though the primary coil, which induces a voltage in each secondary coil in proportion to its mutual inductance with the primary coil. As the core moves along the tube, these mutual inductances change, causing the voltages induced in the secondary coils to change as well. Because the coils are connected in reverse series, the output voltage is the difference between the two secondary voltages. When the core is equidistant between the two secondary coils, equal but opposite voltages are induced in both secondary coils and the output voltage is zero. If the core is displaced in one direction, the voltage in one coil increases as the other decreases, causing the output voltage to increase proportionally to the degree of displacement to one side. If the core moves in the other direction, the voltage will also increase, but in a polarity opposite to that of the primary voltage.

In the present embodiment, the TET coil 104 serves as the primary coil of the LVDT. The "double D" position-sensing coils 106, 108 serve as the secondary coils. The position-sensing coil 106 recognizes displacement along the X-axis, and the position-sensing coil 108 recognizes displacement along the Y-axis. Instead of a ferromagnetic core, the present embodiment uses the IPG's coil 154 to shape the magnetic field around the TET coil 104. The position-sensing coils 106, 108 are mechanically aligned with the TET coil 104 such that equal and opposite voltages are induced in the position-sensing coils 106, 108 when the coil assembly 160 is centered in the corresponding axis upon the IPG coil 154. As the coil assembly 160 moves off center so that IPG coil 154 is closer to one "D" of the position-sensing coil 106 (or 108) and farther from the other, a net AC voltage is induced in that position-sensing coil. The voltage increases in proportion to the displacement of the IPG coil 154 from the center of the position-sensing coil 106 (or 108). This voltage reaches a maximum when the displacement approaches the outer circumference of the TET coil 104, and returns to zero for larger displacements.

Figure 7A:
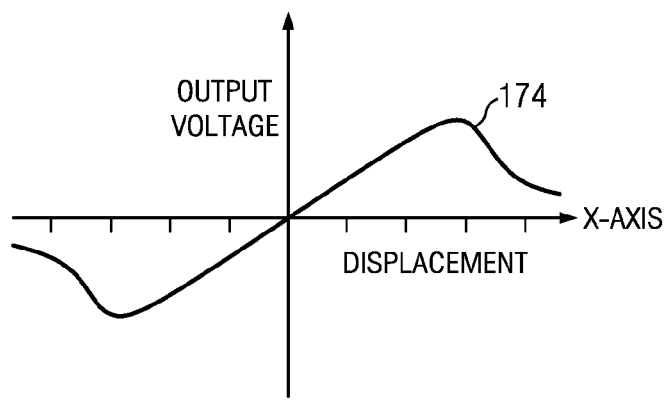
FIGS. 7A and 7B are graphical representations of the output voltage of the synchronous rectifier vs. the transcutaneous energy transfer coil displacement.
Figure 7B:
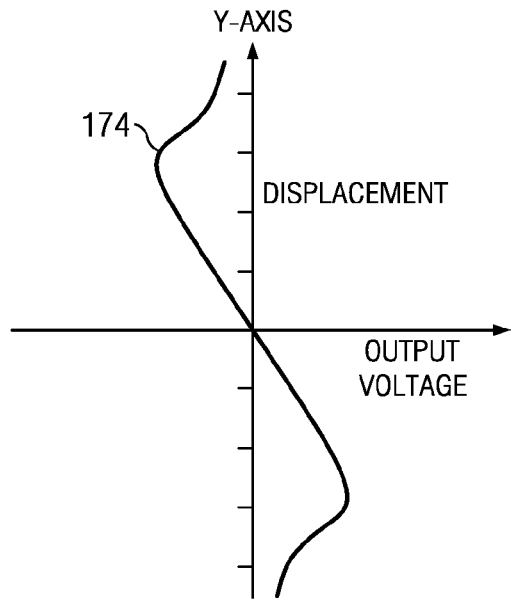

FIGS. 7A and 7B are graphical representations of a set of output voltages from the position sense circuitry 46 of FIG. 2 vs. the transcutaneous energy transfer coil displacement. Rectification of the position-sensing coil 106 (or 108) "double-D" output (driven by the TET coil 104) creates an S-curve 174 relationship between coil displacement in one axis and rectifier output voltage. The voltage is either positive, negative, or zero depending upon the direction and magnitude of the coil displacement. FIG. 7A represents the voltage relative to the displacement in the X-axis, and FIG. 7B represents the voltage relative to the displacement in the Y-axis. As mentioned above, the position-sensing coil 106 recognizes displacement along the X-axis, and the position-sensing coil 108 recognizes displacement along the Y-axis. The dual output of the pair of perpendicularly-oriented position-sensing coils 106, 108 allows the coil assembly 160 to recognize and reflect axial alignment.

Using the S-curves 174 alone to determine coil position and alignment may be inaccurate due to the fact that the output voltage will return to zero as the displacement moves beyond the radius of the position-sensing coils 106, 108 (i.e., when the IPG charging coil 154 is laterally displaced beyond the outer circumference of the position-sensing coils 106, 108). Such large displacements in either the X-axis or Y-axis direction produce a zero voltage rectifier output and may falsely indicate optimal TET coil 104 to IPG coil 154 alignment. This scenario is remedied by circuitry that looks for a zero-crossing event. When a zero-crossing event is detected, a flip-flop is set indicating optimal TET coil 104 to IPG coil 154 alignment in a single axis. A window comparator resets the flip-flop if the voltage moves outside plus/minus limits about zero.

Figure 8:
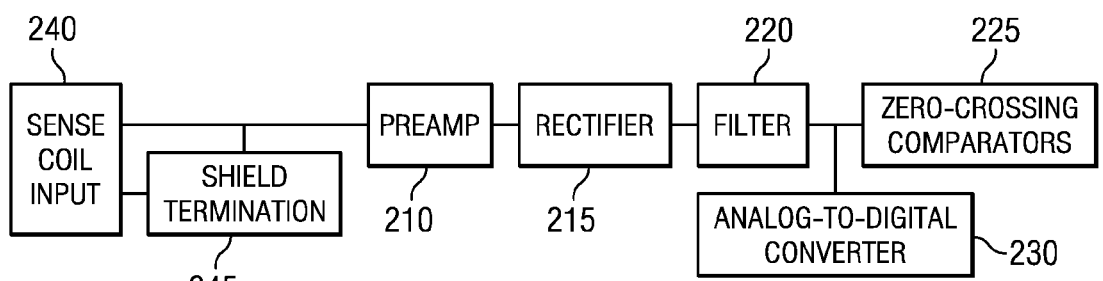
FIG. 8 is a schematic block diagram illustrating the electrical circuitry of one of the position-sensing circuits within the TET device.

FIG. 8 is a schematic block diagram illustrating a portion of the electrical circuitry (e.g., position-sensing circuitry 46 of FIG. 2 or electrical circuitry 109 of FIG. 3) of the coil positioning system. Each of the double-D IPG positioning coils 106, 108 are processed by identical circuits. For this reason only one of such circuit is shown in FIG. 8.

The block diagram shown in FIG. 8 includes a preamplifier section 210, a rectifier section 215, a filter section 220, a comparators section 225, and an analog-to-digital converter section 230. The preamplifier section 210 includes circuitry for amplifying a signal from one of the position-sensing coils 106, 108 (shown in FIGS. 6A-6B), which is shown here as sense coil input component 240. The rectifier section 215 is coupled to the preamplifier section 210 and includes circuitry for converting AC components of the output of the preamplifier section 210 into DC components. The filter section 220 is coupled to the rectifier section 215 and includes circuitry for filtering an output of the rectifier section 215. The comparators section 225 is coupled to the filter section 220 and includes circuitry for, among other things, detecting a zero-crossing event. An analog-to-digital converter section 230 is also coupled to the filter section 220 and is used to provide a digital signal representing the coil assembly 101 displacement in one axis. The output of the analog-to-digital converter section 230 is processed by the processor 47, which would in turn provide instruction to the user via the communication interface 48.

FIGS. 9A and 9B are graphical views of an embodiment of the TET device 100 in accordance with the present disclosure. As shown in these figures, the TET device 100 comprises a handheld battery-operated device that communicates with the IPG 150. The TET device 100 comprises a compact outer housing 278 sized to fit comfortably in the operator's hand. In the illustrated embodiment, the housing 278 is a polyhedron-shaped container configured to contain the various components of the TET device 100. The housing 278 may be alternatively configured to conform to the operator's palm or be configured in a variety of other shapes. In one example, the housing 278 forming the TET device 100 has a thickness of less than about 1.5 inch, a width of less than about 3 inches, and a height of less than about 4 inches. However, both larger and smaller sizes are contemplated. To minimize weight and maximize ease of maneuverability, the housing 278 is constructed of a durable and lightweight material such as plastic. The TET device 100 operates using replaceable and/or rechargeable batteries.

The TET device 100 comprises a flat panel display screen 110. In the illustrated embodiment, the display screen 110 comprises a liquid crystal display ("LCD") (or another suitable portable display) and displays coil alignment when this mode is activated. Alternative embodiments may include buttons that allow the IPG 150 to be turned ON or OFF, provide for the adjustment of various alignment parameters, or provide for the selection of different display screens. Some functions or screens may be accessible through the repeated pushing of particular buttons, pushing various buttons in combination or in a certain sequence, or by pushing buttons for an extended period of time.

In the embodiment shown, the display screen 110 is designed to convey information to the operator about the alignment of the coil assembly 101 to the IPG 150. FIG. 9A illustrates the alignment image of the display screen 110a when the coil assembly 101 and the IPG 150 are not in alignment, and FIG. 9B illustrates the alignment image on the display screen 110b when the coil assembly 101 and the IPG 150 are in alignment. When the TET device 100 is turned on and the coil assembly 101 is moved into proximity with the IPG 150, a representative IPG image 282 is shown fixed in the center of the screen 110. As the operator moves the coil assembly 101 into proximity with the IPG 150, crosshairs 283 (visually representing the coil assembly 101) will appear on the display screen 110 and move around and over the fixed IPG image 282 in a visual representation of the alignment status of the TET coil 104 and the IPG charging coil 154. The distance of the onscreen crosshairs 283 (representing the TET coil 104) from the onscreen IPG image 282 (representing the IPG coil 154) in each of the mutually perpendicular axes is correlated to the voltage output of each of the rectified position-sensing coils 106, 108. For example, this correlation may be calculated by the circuitry section 47 shown in FIG. 2, where voltages measured from the position sense circuitry 46 are converted into digital signals that can be analyzed by the processor 47. The processor 47 is capable of driving the communications interface 48, which in this embodiment is a display screen 110, with a variety of inputs and/or commands. Optimal coil alignment is indicated on the display screen 110b, in FIG. 9B, when the crosshairs 283 are shown centered on and directly superimposed over the representative IPG image 282.

In an embodiment, to achieve optimal coil alignment, the display screen 110 may display visual instructions such as text instructions telling an operator where or how to move the TET coil assembly 101. For example, the text instructions may be, "move the charging device to the right" (or in another suitable direction). The text instructions may be constantly updated until optimum alignment is achieved between the coil assembly 101 and the IPG 150. At that point, the display 110 may display a text indicating optimum alignment has been achieved, and no more movement is necessary. It is understood that in some embodiments, the movement directions may be audible in nature, or may be a combination of audible and visual.

Based on the discussions above, it can be seen that the display 110 advantageously allows the operator to receive real-time visual feedback indicating not only the quality of the coil alignment, but also in which direction they should move the coil assembly 101 to achieve optimal coil alignment. Other types of alignment displays are also contemplated.

Figure 10:
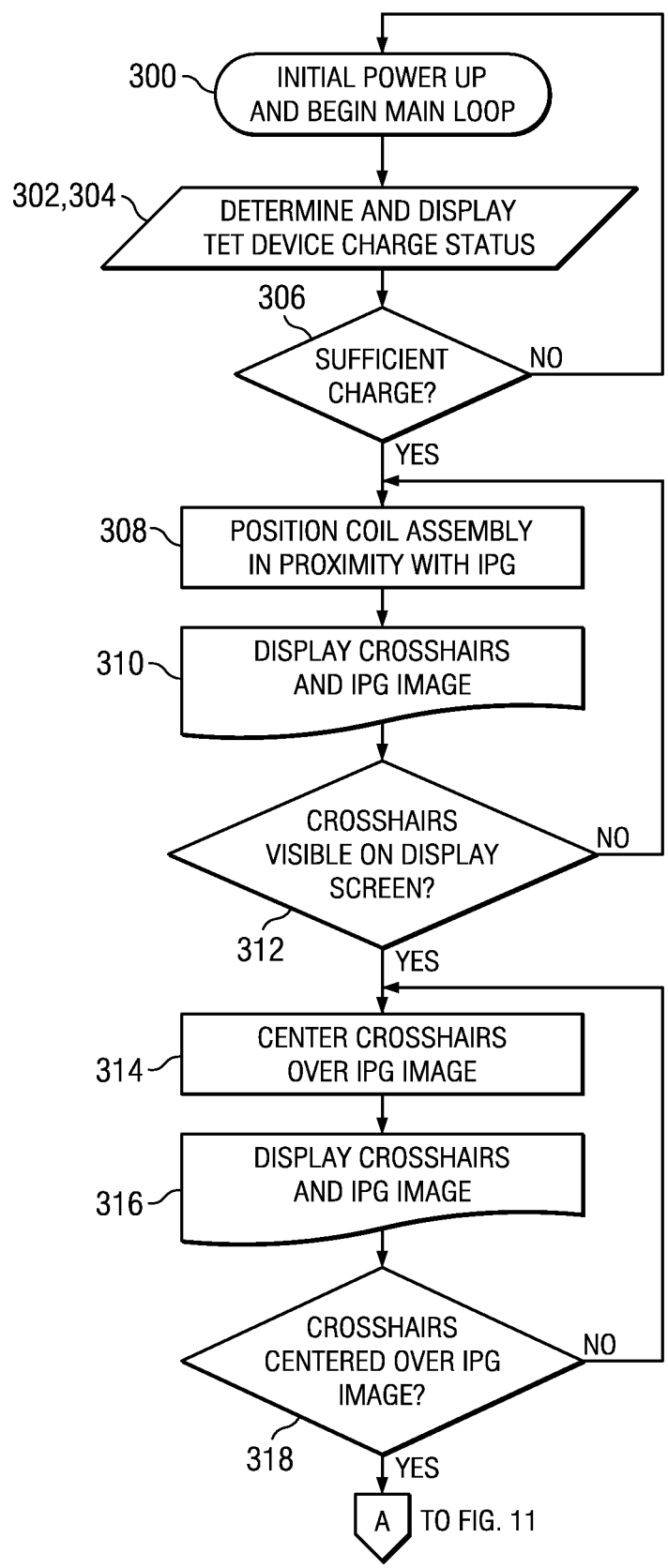
FIGS. 10-11 together depict a flow chart illustrating the alignment and charging of an implantable medical device through the use of a TET device.
Figure 11:
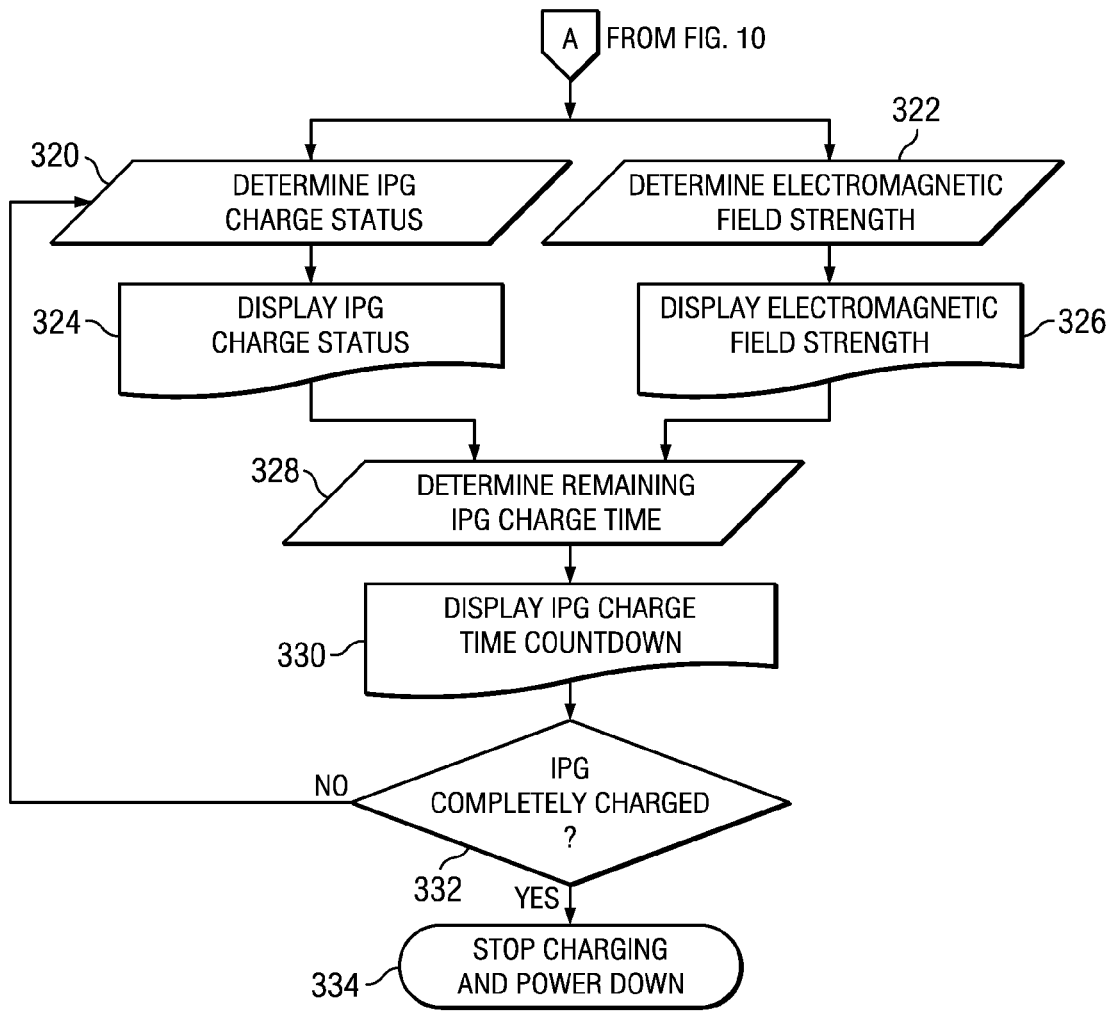

FIGS. 10 and 11 each contain a portion of a flow chart illustrating an exemplary alignment and charging of an implantable medical device using a TET device according to embodiments of the present disclosure. With initial reference to FIG. 10, the TET device 100 is powered up at the start step 300. At step 302, the TET device 100 determines its current charge, and at step 304, the TET device 100 displays that charge status of the TET device battery. At step 306, the TET device 100 determines whether the charge is sufficient to proceed with charging of the IPG 150. If the TET device 100 charge is deemed insufficient, then the TET device 100 continues to be powered up at step 300 and the charge continues to be determined and displayed at steps 302 and 304, respectively, until the TET device 100 charge is deemed sufficient at step 306. Once the TET device 100 charge is deemed to be sufficient, then the operator may position the coil assembly 101 over the skin in proximity with the IPG 150 in step 308. The operator may be guided in this initial placement by visual or tactile signs of implantation, such as a scar, an indentation of the skin, or a bulging area of skin.

When the coil assembly 101 is in proximity with the IPG 150, the display screen 110 displays crosshairs 283 and a representative IPG image 282 in step 310. The representative IPG image 282 remains fixed in the center of the display while the crosshairs 283 (representative of the TET coil 104) move in relation to the degree of lateral displacement of the TET coil 104 from the IPG coil 154. At step 312, the operator must ascertain whether the crosshairs 283 are displayed on the display screen 110. If the crosshairs 283 are not visible, this indicates that the coil assembly 101 is not positioned in proximity with the IPG 150 and the operator must then reposition the coil assembly 101 in proximity with the IPG 150. If the crosshairs 283 are visible, the coil assembly 101 is located in proximity with the IPG 150 and the operator may then move the coil assembly 101 until the crosshairs 283 are displayed as centered on and superimposed over the representative IPG image 282 in steps 314 and 316. At step 318, the operator must evaluate whether the crosshairs 283 are centered on over the representative IPG image 282. If the operator does not see the crosshairs 283 centered on the representative IPG image 282, then the operator must return to step 314 and move the coil assembly 101 until the crosshairs 283 are displayed as centered on and superimposed over the representative IPG image 282 in step 316.

Proceeding to FIG. 11, if the operator determines that the crosshairs 283 are centered over the representative IPG image 282, then the TET device 100 will simultaneously determine the existing charge status of the IPG 150 at step 320 and determine the electromagnetic field strength generated by the coil assembly 101 and the IPG charging coil 154 at step 322. The TET device 100 then displays the existing charge status of the IPG in step 324 and displays the electromagnetic field strength in step 326. In step 328, the TET device 100 determines the remaining IPG charge time, then displays the remaining IPG charge time in step 330. At step 332, the TET device 100 must evaluate whether the IPG 150 is completely charged. If the IPG 150 is not completely charged, the TET device 100 must continue to charge the IPG 150 with the coil assembly 101 held stationary above the IPG 150. If the IPG 150 is completely charged, the TET device 100 will stop charging the IPG 150 and the operator may remove the coil assembly 101 and power down the TET device 100 at step 334.

FIG. 12 is a flowchart illustrating an operational method 500 of the TET device described above. The method 500 includes block 510, which a coil assembly is provided. The coil assembly includes a primary coil and a plurality of position-sensing coils. The method 500 includes block 520 in which an electrical parameter of the coil assembly is measured. The method 500 includes block 530 in which positional information of the coil assembly is determined relative to the implanted medical device. The method 500 includes block 540 in which the positional information is communicated. The communication may be done through a communication interface, which may include a visual display.

Figure 13A:
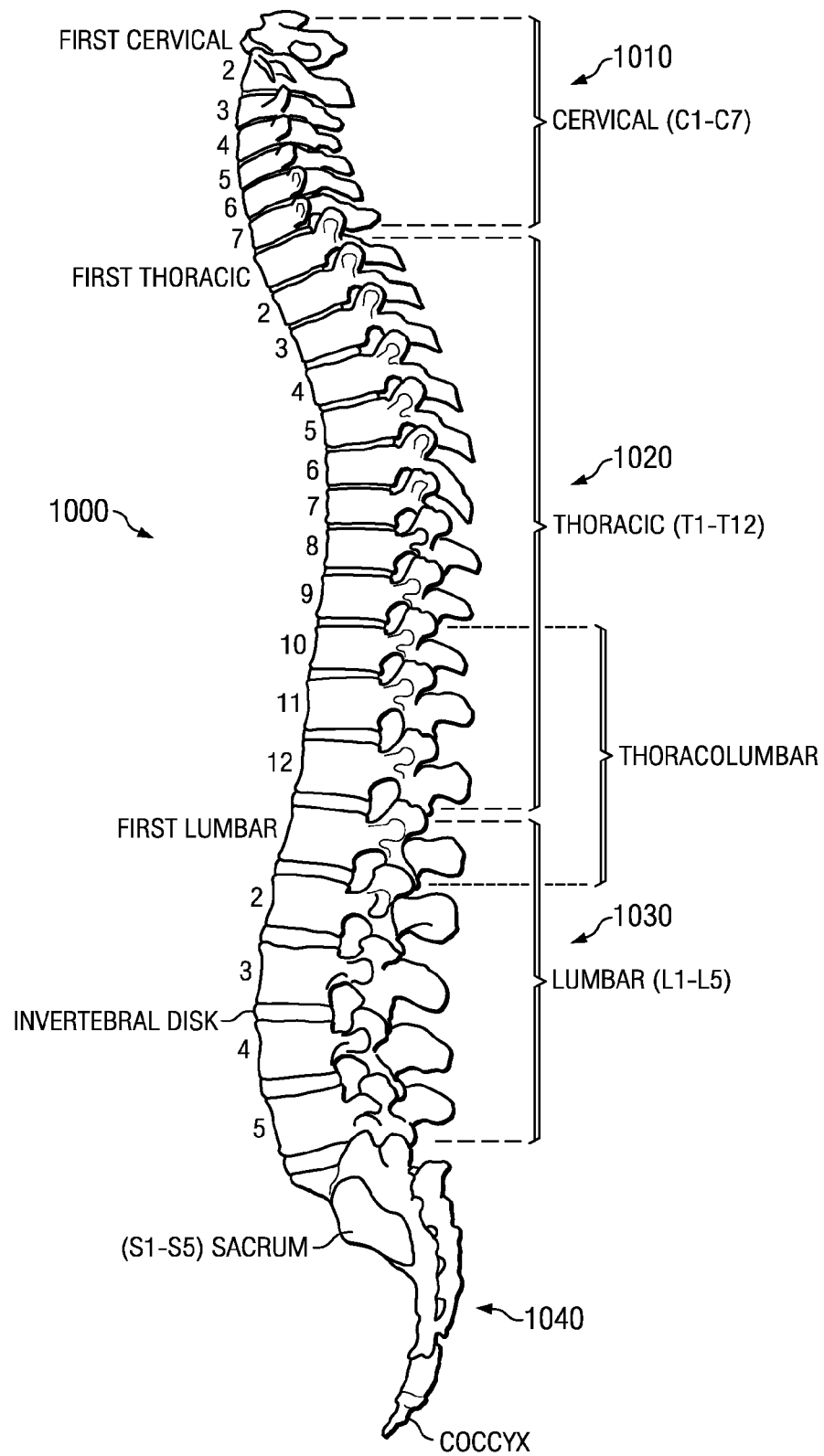
FIGS. 13A and 13B are side and posterior views of a human spine, respectively.
Figure 13B:
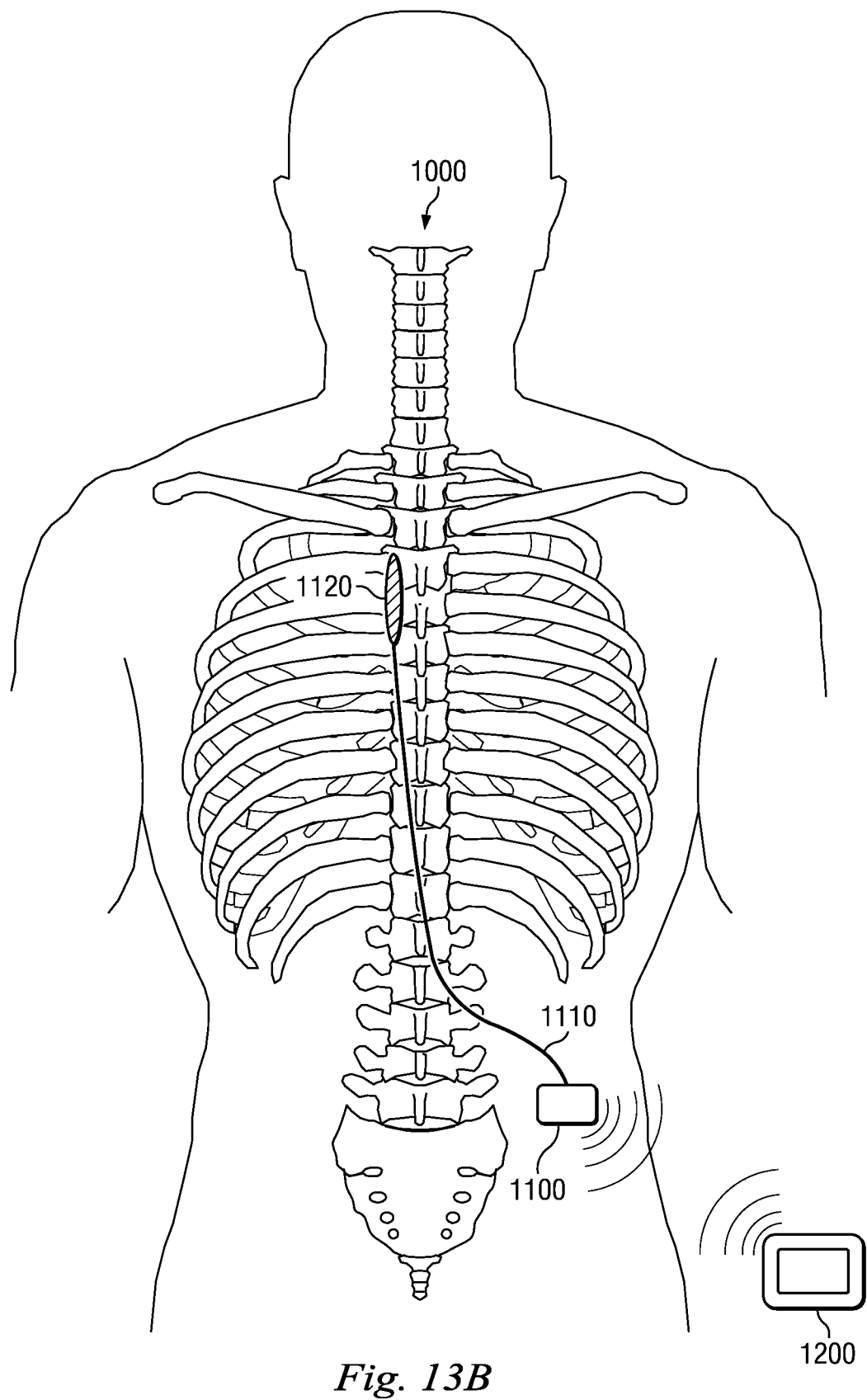

FIG. 13A is a side view of a spine 1000, and FIG. 13B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 13B, an IPG device 1100 is shown implanted inside the body and communicating with a TET device 1200. The IPG device 1100 may include various embodiments of the IPG 150 described above. The TET device 1200 may include various embodiments of the TET device 100 described above. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. The distal end of the lead 1110 with its accompanying electrodes may be positioned beneath the dura mater using well-established and known techniques in the art.

The electrodes 1120 deliver current drawn from the IPG device 1100, therefore generating an electric field near the neural tissue. The electric field stimulates the neural tissue to accomplish its intended functions. For example, the neural stimulation may alleviate pain in an embodiment. In other embodiments, a stimulator as described above may be placed in different locations throughout the body and may be programmed to address a variety of problems, including for example but without limitation: prevention or reduction of epileptic seizures, weight control or regulation of heart beats.

It is understood that the IPG 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. As is apparent in FIG. 13B, the IPG 1100 may be able to communicate with and be charged by the TET device 1200.

The devices, systems, and methods described herein provide an improved and more accurate system of positioning a TET device over and charging an IPG implanted in a patient by providing the operator with a visual indication of the direction in which the TET device needs to be moved in order to obtain the perfect alignment between a TET coil and an IPG charging coil. The TET device as described herein also enables a constant monitoring of the efficiency of the energy transfer from the TET coil and the IPG charging coil.

Applicants note that the procedures disclosed herein are merely exemplary and that the systems and methods disclosed herein may be utilized for numerous other medical processes and procedures. Although several selected embodiments have been illustrated and described in detail, it will be understood that they are exemplary, and that a variety of substitutions and alterations are possible without departing from the spirit and scope of the present disclosure, as defined by the following claims.

What is claimed is:

1. A charger for an implanted medical device, the charger comprising:
    a power supply;

a coil assembly electrically coupled to the power supply, the coil assembly including a primary coil and a plurality of sense coils, wherein at least two of the sense coils are perpendicularly oriented with respect to one another;

electrical circuitry configured to:

measure electrical parameters of the coil assembly; and determine, based on the measured electrical parameters, locational information with respect to the coil assembly and the implanted medical device; and a visual interface configured to visually communicate the locational information.

2. The charger of claim 1, wherein the sense coils are located in different layers of a substrate.

3. The charger of claim 1, wherein the primary coil is located over the sense coils.

4. The charger of claim 1, wherein the electrical parameters comprise voltages of one or more of the sense coils.

5. The charger of claim 1, wherein the electrical circuitry is configured to calculate, based on the measured electrical parameters, a locational offset between the coil assembly and the implanted medical device.

6. The charger of claim 1, wherein the electrical circuitry comprises:

amplification circuitry configured to amplify electrical signals from the sense coils;

rectification circuitry configured to convert AC components of an output of the amplification circuitry into DC components; and filtering circuitry configured to filter an output of the rectification circuitry.

7. The charger of claim 6, wherein the electrical circuitry further comprises comparator circuitry coupled to the filtering circuitry, the comparator circuitry being configured to detect a zero-crossing event.

8. The charger of claim 1, wherein the visual interface is configured to display, on a screen, a first visual object representing a location of the coil assembly and a second visual object representing a location of the implanted medical device.

9. The charger of claim 8, wherein the visual interface is configured to update the locations of the coil assembly and the implanted medical device in real time in response to actual movements of the coil assembly or the implanted medical device.

10. The charger of claim 1, wherein the visual interface is configured to communicate instructions to a user to align the coil assembly with the implanted medical device.

11. A method for charging an implanted medical device, comprising:

providing a coil assembly, the coil assembly including a primary coil and a plurality of sense coils, wherein at least two of the sense coils are perpendicularly oriented with respect to one another;

measuring electrical parameters of the coil assembly;

determining, based on the measured electrical parameters, locational information with respect to the coil assembly and the implanted medical device; and communicating the locational information via a visual interface.

12. The method of claim 11, wherein the sense coils are located in different layers of a substrate, and wherein the primary coil is located over the sense coils.

13. The method of claim 11, wherein the measuring of the electrical parameters comprises measuring voltages of one or more of the sense coils.

14. The method of claim 11, wherein the determining comprises calculating, based on the measured electrical parameters, a locational offset between the coil assembly and the implanted medical device.

15. The method of claim 11, wherein the determining comprises:

amplifying electrical signals from the sense coils;

converting AC components of the amplified electrical signals into DC components;

filtering the DC components of the amplified electrical signals; and detecting a zero-crossing event based on the filtered DC components.

16. The method of claim 11, wherein the communicating comprises displaying, on a screen, a first visual object representing a location of the coil assembly and a second visual object representing a location of the implanted medical device.

17. The method of claim 11, wherein the communicating comprises communicating instructions to a user to align the coil assembly with the implanted medical device.

18. A medical system, comprising:

an implantable medical device; and a charger for charging the implantable medical device, wherein the charger includes: a coil assembly, circuitry that is electrically coupled to the coil assembly, and a communications interface, wherein:

the coil assembly includes:

a primary coil;

a first position-sensing coil; and a second position-sensing coil that is perpendicularly oriented with respect to the first position-sensing coil;

the circuitry is configured to:

measure voltages of the first and second position-sensing coils; and determine, based on the measured voltages, locational information with respect to the coil assembly and the implantable medical device; and the communications interface is configured to visually communicate the locational information.

19. The medical charging system of claim 18, wherein the circuitry comprises:

amplification circuitry configured to amplify electrical signals from the sense coils;

rectification circuitry configured to covert AC components of an output of the amplification circuitry into DC components;

filtering circuitry configured to filter an output of the rectification circuitry; and comparator circuitry coupled to the filtering circuitry, the comparator circuitry being configured to detect a zero-crossing event based on the filtered output of the rectification circuitry.

20. The medical charging system of claim 18, wherein the communications interface is configured to display, in real time, a first visual object representing a location of the coil assembly and a second visual object representing a location of the implantable medical device.

* * * * *